United States Patent [19]

Sepetka

[11] Patent Number: 5,234,437
[45] Date of Patent: Aug. 10, 1993

[54] DETACHABLE PUSHER-VASOOCCLUSION COIL ASSEMBLY WITH THREADED COUPLING

[75] Inventor: Ivan Sepetka, Redwood City, Calif.

[73] Assignee: Target Therapeutics, Inc., Fremont, Calif.

[21] Appl. No.: 806,898

[22] Filed: Dec. 12, 1991

[51] Int. Cl.⁵ .................................. A61B 17/00
[52] U.S. Cl. .................... 606/108; 606/194; 128/772; 604/158
[58] Field of Search ............ 606/109, 191, 194, 198, 606/200; 604/158, 170, 281, 282; 128/656, 654, 772

[56] References Cited

U.S. PATENT DOCUMENTS

| | | | |
|---|---|---|---|
| 3,868,956 | 3/1975 | Alfida et al. | 606/108 |
| 4,494,531 | 1/1985 | Gianturco | 606/200 |
| 4,503,569 | 3/1985 | Dotter | 606/200 |
| 4,795,458 | 1/1989 | Regan | 606/191 |
| 5,037,427 | 8/1991 | Harada et al. | 606/108 |
| 5,089,005 | 2/1992 | Harada | 606/194 |
| 5,098,374 | 3/1992 | Othel-Jacobsen et al. | 604/8 |

*Primary Examiner*—Edgar S. Burr
*Assistant Examiner*—Christopher A. Bennett
*Attorney, Agent, or Firm*—Morrison & Foerster

[57] ABSTRACT

A pusher-vasoocclusive coil assembly that is advanced through a catheter to a site within a vessel and is manipulated to detach the coil from the assembly. The pusher has a distal end that is initially threaded into the proximal end of the coil and the assembly includes a sleeve that is slid over the pusher and whose distal edge abuts the proximal end of the coil to hold the coil in place while the distal end of the pusher is threaded out of the coil to detach the coil at the site.

14 Claims, 2 Drawing Sheets

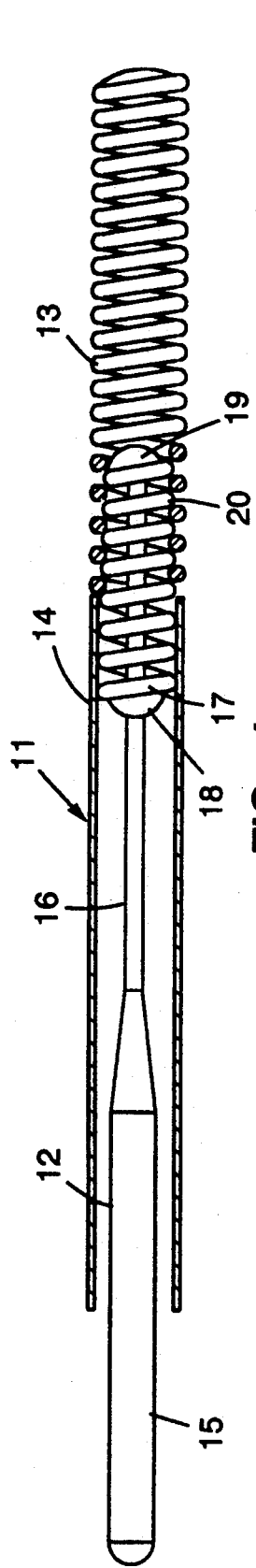
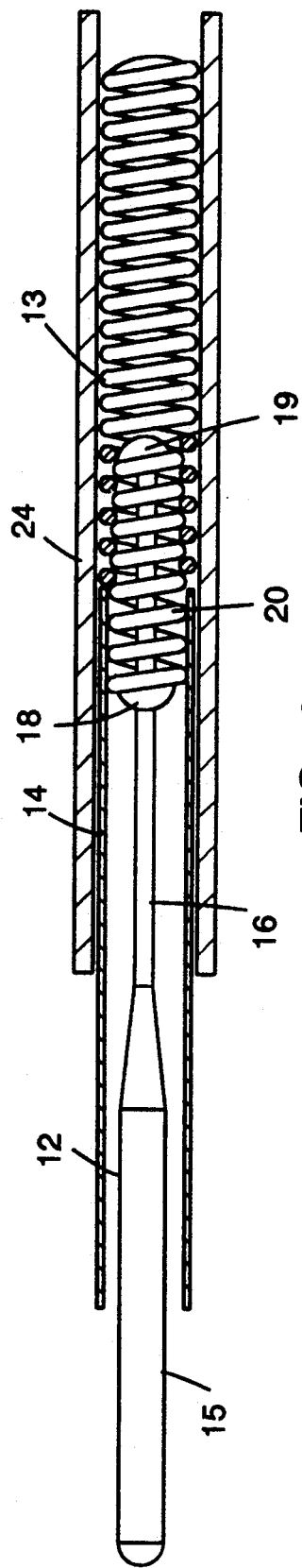
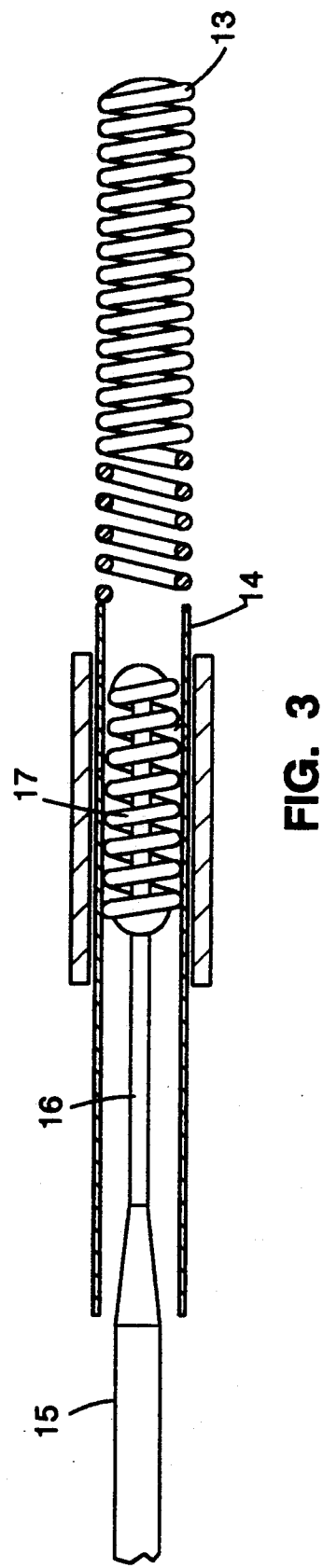

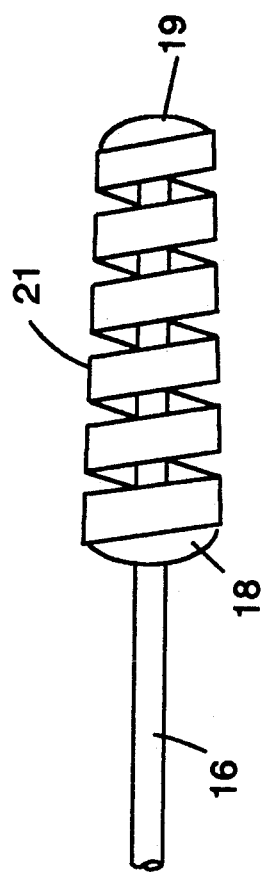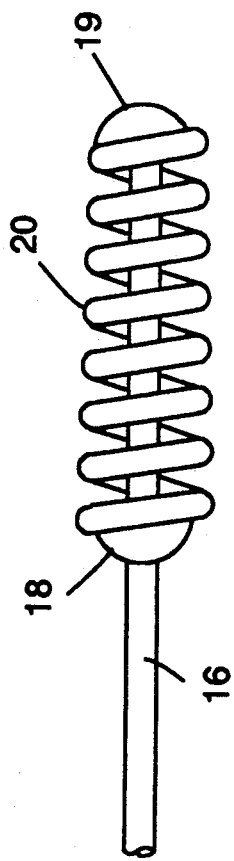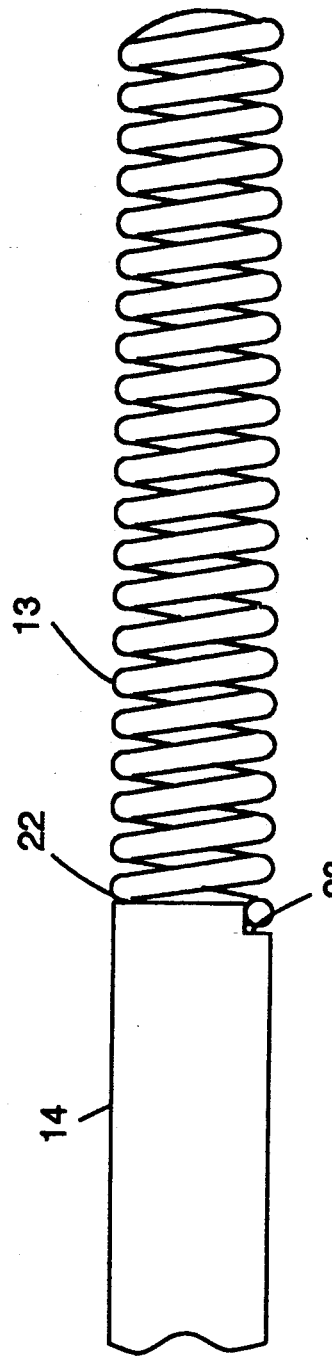

DETACHABLE PUSHER-VASOOCCLUSION COIL ASSEMBLY WITH THREADED COUPLING

TECHNICAL FIELD

The present invention is in the general field of surgical instruments and relates specifically to an apparatus for delivering a vasoocclusion coil to a selected site within a vessel (e.g., an aneurysm) via a catheter.

BACKGROUND

Vasoocclusion coils or wires are used to occlude a site, such as an aneurysm, within a vessel. The coils may be of a regular (e.g., helical) configuration or assume a random convoluted configuration at the site. Vasoocclusion coils are described in U.S. Pat. No. 4,994,069. The coils are normally made of a radioopaque, biocompatible metal such as platinum, gold, or tungsten. In treating aneurysms it is common to place a plurality, typically 4 to 12, coils within the aneurysm. The coils occlude the site by posing a physical barrier to blood flow and by promoting thrombus formation at the site.

The coil(s) have typically been placed at the desired site using a catheter and a pusher. The site is first accessed by the catheter. In treating peripheral or neural conditions requiring occlusion, the sites are accessed with flexible, small diameter catheters such as the catheters described in U.S. Pat. Nos. 4,739,768 and 4,813,934. The catheter may be guided to the site through the use of guidewires (see U.S. Pat. No. 4,884,579) and/or flow-directed means such as balloons at the distal end of the catheter. Once the site has been accessed, the catheter lumen is cleared (i.e., the guidewire is removed if a guidewire has been used), the coil is placed in the proximal end of the catheter and is advanced through the catheter with a pusher. Pushers are wires having a distal end that is adapted to engage and push the coil distally as the pusher is advanced through the catheter. When the coil reaches the distal end of the catheter it is plunged therefrom by the pusher into the vessel. This technique of plunging the coil from the distal end of the catheter has undesirable limitations. First, because of the plunging action, the positioning of the coil at the site cannot be controlled to a fine degree of accuracy. Second, once plunged from the catheter, it is difficult to reposition or retrieve the coil if desired. Indeed, another device, called a retriever, must be threaded through the catheter to snare the coil to reposition or retrieve it.

In view of these limitations, techniques have recently been developed to enable more accurate placement of coils within a vessel. In one technique (described in U.S. patent application Ser. No. 492,717, filed Mar. 13, 1990) the coil is bonded via a metal-to-metal joint to the distal end of a pusher made of a different metal than the coil. The coil-carrying pusher is advanced through the catheter to the site and a low electrical current is passed through the pusher-coil assembly. The current causes the joint between the pusher and coil to be severed via electrolysis. The pusher may then be retracted leaving the detached coil at an exact position within the vessel. In addition to enabling more accurate coil placement, the electric current may facilitate thrombus formation at the coil site. The only perceived disadvantage of this method is that the electrolytic release of the coil requires a given time period so that rapid detachment of the coil from the pusher is not possible. In another technique the confronting ends of the pusher and coil are designed such that the pusher clamps onto the wire and holds it until the clamp is released. Accordingly, this methodology utilizes a mechanical detachment mechanism rather than an electrolytic mechanism.

A primary object of the present invention is to provide an alternative mechanical means for detaching a vasoocclusive coil from a pusher at a desired vessel site.

DISCLOSURE OF THE INVENTION

One aspect of the invention is a detachable pusher-vasoocclusive coil assembly for use in occluding a selected site within a vessel comprising in combination: (a) a vasoocclusive coil having a proximal end that defines a helical coil; and (b) a pusher having a distal end that is threadedly coupled to the helical coil. In a preferred embodiment the assembly includes (c) means for holding the proximal end of the vasoocclusive coil in place while the distal end of the pusher is threaded out of engagement with the helical coil. Said means may be a sleeve that (i) is received coaxially about the pusher, (ii) has a smaller inner diameter than the outer diameter of the helical coil, and (iii) has a distal edge that is adapted to abut the proximal end of the vasoocclusive coil.

Another aspect of the invention is a method for occluding a selected site within a vessel comprising the steps of:

(a) accessing the site with a distal end of a catheter;

(b) advancing the above-described pusher-coil assembly through the catheter so as to position the vasoocclusive coil of the assembly at the site free of the distal end of the catheter; and (c) threading the distal end of the pusher out of engagement with the proximal end of the vasoocclusive coil.

BRIEF DESCRIPTION OF THE DRAWINGS

In the drawings, which are not to scale:

FIG. 1 is a partly sectional enlarged elevational view of one embodiment of the pusher-vasoocclusive coil assembly of the present invention.

FIG. 2 is a partly sectional enlarged elevational view of the assembly of FIG. 1 within a catheter.

FIG. 3 is a partly sectional enlarged elevational view of the assembly and catheter of FIG. 2 showing the vasoocclusive coil disengaged from the pusher.

FIG. 4 is an enlarged elevational view of the distal end of the pusher of FIG. 1.

FIG. 5 is an enlarged elevational view of alternative design of the distal end of the pusher.

FIG. 6 is an enlarged elevational view of an alternative design of the sleeve of the assembly that abuts the proximal end of the coil.

In the drawings proximal is left and distal is right. Like parts are referred to by the same reference numeral in the drawings.

MODES FOR CARRYING OUT THE INVENTION

FIG. 1 depicts one embodiment of a pusher-vasooclusive coil assembly, generally designated 11, of the invention. The assembly comprises three main elements; a pusher, generally designated 12; a vasoocclusive coil 13, and a sleeve 14.

Coil 13 is shown in FIG. 1 as a uniform diameter helical coil wire. All that is required, however, for the present invention is that its proximal end defines a helical coil and that overall it be of such a configuration that it may be advanced through a catheter of the dimensions required to access the desired vessel site. Thus, the distal segment of the coil may be regularly or randomly configured. Coil 13 is made of a radioopaque biocompatible metal, such as platinum, gold or tungsten so that its location within the vessel may be viewed radiographically. For use in occluding peripheral or neural sites the coils will typically be made of 0.05 to 0.15 mm diameter platinum wire that is wound to have an inner diameter of 0.15 to 0.96 mm with a minimum pitch (i.e., the windings are close or tight). The length of the wire (wound) will normally be in the range of 0.5 to 60 cm, preferably 2 to 20 cm. As indicated, if desired, the distal segment of the coil may be formed so that the coil takes an essentially linear configuration in which it may be advanced through the catheter and assume a randomly oriented relaxed condition after it is released from the catheter (see U.S. Pat. No. 4,994,069).

Pusher 12 comprises a proximal end segment 15 that provides a means by which the pusher may be gripped and manipulated, a main central core 16 in the form of a thin wire or rod (core 16 is much longer than depicted in the drawings), and a tapered coil distal tip 17. The entire length of the pusher will be such as to be capable of being advanced entirely through the catheter to the vessel site with a sufficient portion of segment 15 protruding from the proximal end of the catheter to enable the pusher to be manipulated (see FIGS. 2 and 3). Typically, the core segment will constitute at least about 90-95% of the entire length of the pusher. For use in peripheral or neural surgeries, the pusher will normally be about 100 to 200 cm in length, more usually 160 to 180 cm in length. The diameter of the core 16 of the pusher will typically be in the range of 0.25 to 0.90 mm.

As shown in FIG. 4 tip 17 of the pusher is composed of a first radial enlargement 18 on core 16, a second radial enlargement 19 at the very end of the core, and a helical coil 20 that extends between enlargements 18 and 19 about core 16. The enlargements will normally be formed of solder or brazing. The proximal end of coil 20 is affixed to enlargement 18 and the distal end of coil 20 is affixed to enlargement 19. Solder, brazing or suitable adhesives may be used to achieve such affixation. Coil 20 tapers distally, from large to small diameter. Such tapering facilitates the threading of the coil into the proximal end of the vasoocclusive coil to couple the pusher and coil. In this regard the diameter of coil 20 at the distal end thereof is dimensioned to be received within the proximal end of the vasoocclusive coil in threaded relationship as shown in FIGS. 1 and 2. Typically the diameter will be from about 0.20 to 0.90 mm at enlargement 18 and about 0.16 to 0.60 mm at enlargement 19. The outer diameter of coil 20 at enlargement 18 is less than the inner diameter of the proximal end of the vasoocclusive coil.

FIG. 5 illustrates an alternative pusher tip design. The design of FIG. 5 is identical to the tip of FIG. 4 except that the circular cross-section coil 20 of FIG. 4 is replaced with a flat ribbon (rectangular cross-section) coil 21. Otherwise the two tips are identical in structure and function.

While the embodiments shown in the drawings depict the pusher and coil threadably coupled in a manner in which the distal end of the pusher is threaded into the lumen of the coil with the inner surfaces of the coil windings functioning as interior threads so as to form a coaxial threaded relationship, other embodiments wherein the respective windings of the two coils interfit between one another in substantially the same axial plane rather than interfitting in a coaxial relationship are included within the invention. In the coaxial threaded relationships it is desirable but may not be necessary to employ a coaxial sleeve 14 to hold the coil in place as the vasoocclusive coil may create enough friction against the vessel wall to prevent the coil from rotating when the pusher is threaded out of engagement with the coil. In embodiments wherein the threads interlock in the same axial plane, a coaxial sleeve 14 which holds the coil in place must be used.

Sleeve 14 exemplifies means by which the vasoocclusive coil may be held in place while the tip 17 is threaded out of the proximal end of the vasoocclusive coil to disengage or uncouple the coil and pusher. The inner diameter of sleeve 14 is larger than the largest outer diameter of tip 17 so that the pusher may be moved axially within the sleeve (see FIGS. 1 and 2), but smaller than the outer diameter of the proximal end of the vasoocclusive coil. The inner diameter of the sleeve will normally be 0.30 to 0.95 mm. Thus, when the sleeve is advanced distally its distal edge 22 will abut the proximal end of the vasoocclusive coil. This abutting relationship places a distally directed axial force on the proximal end of the vasoocclusive coil which serves to hold same in place (prevent or retard axial movement and rotation) while the tip 17 is threaded out of the proximal end of the coil by twisting the pusher. The outer diameter of sleeve 14 is small enough that the sleeve may be advanced axially through the catheter.

FIG. 6 shows an alternative design of the distal edge 22 of the sleeve. In the design of FIG. 6 edge 22 has a notch or step 23 that is dimensioned to engage the proximal end of coil 13 in an interlocking relationship to facilitate preventing coil 13 from rotating when tip 17 is threaded out of engagement therewith. Otherwise, the sleeve of FIG. 6 is identical in structure and function to the sleeve of FIG. 1.

Assembly 11 is used to place one or more vasoocclusive coils at a selected site in a vessel as follows. The pusher 12 and coil 13 are assembled as shown in FIG. 1 with tip 17 of the pusher threaded into the proximal end of the vasoocclusive coil. A catheter 24 (FIGS. 2 and 3) is inserted through the vessel lumen (not shown) to the site to be occluded. As indicated previously, conventional catheter insertion procedures involving guidewires and/or flow-directed means may be used to access the site with the catheter. Once the distal end of the catheter is positioned at the site (its location may be determined by coating the end of the catheter with a radioopaque material or otherwise affixing such a material to the distal end of the catheter or incorporating such a material into the distal end of the catheter), the catheter is cleared (i.e., if a guidewire has been used, it is removed) and the pusher-coil assembly is advanced through the catheter 24 (see FIG. 2). Sleeve 14 may be advanced through the catheter simultaneously with the pusher-coil assembly or subsequently in a separate step so that its distal edge 22 abuts the proximal end of the vasoocclusive coil. The assembly is then advanced distally so that the coil is free and clear of the distal end of the catheter (FIG. 3). Then while holding the distal edge of sleeve 14 firmly against the vasoocclusive coil the tip of the pusher is threaded out of the proximal end of the vasoocclusive coil to thus detach the coil and release it at the site. If additional coils need to be placed at the site, the pusher is retracted and the procedure is repeated. After the desired number of coils have been placed at the site, the pusher, sleeve, and catheter are withdrawn from the vessel.

Modifications of the above-described modes for carrying out the invention that are obvious to those of skill in the mechanical and surgical instrument design arts and related fields are intended to be within the scope of the following claims.

I claim:

1. A detachable pusher-vasoocclusive coil assembly for use in occluding a vessel at a selected site within a vessel comprising in combination:
   (a) a vasoocclusive coil having a proximal end that defines a helical coil; and
   (b) a pusher having a threaded distal end that is threaded into said helical coil prior to insertion of said assembly into a vessel and said pusher is unthreaded from said helical coil subsequent to said insertion.

2. The assembly of claim 1 including:
   (c) means for holding the proximal end of the vasoocclusive coil in place while the distal end of the pusher is threaded out of engagement with said helical coil.

3. The assembly of claim 1 wherein the threaded distal end of the pusher is within and in a coaxial relationship with the helical coil.

4. The assembly of claim 2 wherein the threaded distal end of the pusher is a coil interfitting substantially with the helical coil.

5. The assembly of claim 3 wherein the distal end of the pusher defines a tapered coil.

6. The assembly of claim 5 wherein the tapered coil has a circular cross-section.

7. The assembly of claim 2 wherein the means is a sleeve that (i) is received coaxially about the pusher, (ii) has a smaller inner diameter than the outer diameter of the helical coil, and (iii) has a distal edge which edge abuts the proximal end of the helical coil.

8. The assembly of claim 7 wherein said sleeve distal edge abutting the proximal end of the helical coil has a step that interlocks with the proximal end of the helical coil to prevent the helical coil from rotating.

9. The assembly of claim 5 wherein the tapered coil has a rectangular cross-section.

10. A method for occluding a selected site within a vessel comprising the steps of:
    (a) accessing the site with a distal end of a catheter;
    (b) advancing an assembly, in combination, of a vasoocclusive coil having a proximal end that defines a helical coil and a pusher having a threaded distal end which is threaded into said helical coil prior to insertion of said assembly into a vessel and is unthreaded from said helical coil subsequent to said insertion, through the catheter so as to position the vasoocclusive coil at the site and free of the distal end of the catheter;
    (c) threading the distal end of the pusher out of engagement with the proximal end of the vasoocclusive coil; and
    (d) withdrawing the catheter, pusher and said means from the vessel.

11. A method for occluding a selected site within a vessel comprising the steps of:
    (a) accessing the site with a distal end of a catheter;
    (b) advancing an assembly, in combination, of a vasoocclusive coil having a proximal end that defines a helical coil and a pusher having a distal end that is a coil and is threaded into said helical coil prior to insertion of the assembly into a vessel and is unthreaded from said helical coil subsequent to said insertion and means for holding the proximal end of the vasoocclusive coil in place while the distal end of the pusher is unthreaded from said helical coil, through the catheter so as to position the vasoocclusive coil at the site and free of the distal end of the catheter;
    (c) holding the proximal end of the vasoocclusive coil in place with said means while threading the distal end of the pusher out of engagement with the proximal end of the vasoocclusive coil; and
    (d) withdrawing the catheter, pusher and said means from the vessel.

12. A method for occluding a selected site within a vessel comprising the steps of:
    (a) accessing the site with a distal end of a catheter;
    (b) advancing an assembly, in combination, of a vasoocclusive coil having a proximal end that defines a helical coil and a pusher having a distal end that is a coil and is threaded into a coaxial relationship with the helical coil, through the catheter so as to position the vasoocclusive coil at the site and free of the distal end of the catheter;
    (c) threading the distal end of the pusher out of engagement with the proximal end of the vasoocclusive coil; and
    (d) withdrawing the catheter, pusher and said means from the vessel.

13. A method for occluding a selected site within a vessel comprising the steps of:
    (a) accessing the site with a distal end of a catheter;
    (b) advancing an assembly, in combination, of a vasoocclusive coil having a proximal end that defines a helical coil and a pusher having a distal end that is a coil and is threaded into said helical coil prior to insertion of said assembly into a vessel and is unthreaded from said helical coil subsequent to said insertion and means for holding the proximal end of the vasoocclusive coil in place while the distal end of the pusher is threaded into said helical coil, said means comprising a sleeve that is received coaxially about the pusher, has a smaller inner diameter than the outer diameter of the helical coil and has a distal edge which distal edge abuts the proximal end of the helical coil, through the catheter so as to position the vasoocclusive coil at the site and free of the distal end of the catheter;
    (c) holding the proximal end of the vasoocclusive coil in place with said sleeve while threading the distal end of the pusher out of engagement with the proximal end of the vasoocclusive coil; and
    (d) withdrawing the catheter pusher and said means from the vessel.

14. A method for occluding a selected site within a vessel comprising the steps of:
    (a) accessing the site with a distal end of a catheter;
    (b) advancing an assembly, in combination, of a vascular coil having a proximal end that defines a helical coil and a pusher having a distal end that is a coil and is threaded into said helical coil prior to insertion of said assembly into a vessel and unthreaded from said helical coil subsequent to said insertion and means for holding the proximal end of the vasoocclusive coil in place while the distal end of the pusher is unthreaded from said helical coil, said means comprising a sleeve that is received coaxially about the pusher, has a smaller inner diameter than the outer diameter of the helical coil and has a distal edge which distal edge abuts the proximal end of the helical coil, and has a step that interlocks with the proximal end of the helical coil to prevent the helical coil from rotating through the catheter so as to position the vasoocclusive coil at the site and free of the distal end of the catheter;

(c) holding the proximal end of the vasoocclusive coil in place with said sleeve while threading the distal end of the pusher out of engagement with the proximal end of the vasoocclusive coil; and (d) withdrawing the catheter pusher and said means from the vessel.

* * * * *